United States Patent [19]

Downing

[11] Patent Number: 4,940,323
[45] Date of Patent: Jul. 10, 1990

[54] LIGHT TESTING AND STIMULATING DEVICE EMPLOYING VARIABLE FREQUENCY INTERRUPTED LIGHT SOURCE AND COLOR FILTERS

[76] Inventor: John C. Downing, 156 Bahama Reef, Novato, Calif. 94949

[21] Appl. No.: 253,900

[22] Filed: Oct. 4, 1988

Related U.S. Application Data

[63] Continuation of Ser. No. 61,891, Jun. 15, 1987, abandoned.

[51] Int. Cl.⁵ ............................................. A61B 3/00
[52] U.S. Cl. ................................. 351/203; 351/222; 351/242
[58] Field of Search ............... 351/234, 235, 242, 200, 351/201, 203, 211, 221, 222

[56] References Cited

U.S. PATENT DOCUMENTS

| | | |
|---|---|---|
| 2,057,983 | 10/1934 | Spitler . |
| 2,089,863 | 8/1937 | Updegrave . |
| 2,262,217 | 11/1938 | Wottring . |
| 3,277,888 | 10/1965 | Otwell . |
| 3,910,690 | 10/1975 | Regan ................................ 351/242 |
| 4,522,474 | 6/1985 | Slavin ................................ 351/203 |
| 4,550,990 | 11/1985 | Trispel et al. ..................... 351/222 |

*Primary Examiner*—Paul M. Dzierzynski
*Attorney, Agent, or Firm*—David Pressman

[57] ABSTRACT

A light stimulator device which tests and therapeutically stimulates the neurovisual system by visible light. It utilizes a balanced spectrum, magnetic, plasmatic light source (32) with different color filters (20) and different apertures (18) interposed between the light source and the subject's eyes. The flash rate of the light source (32) can be continuously varied (24) to provide for diagnostic CFF testing.

25 Claims, 4 Drawing Sheets

INCANDESCENT
THROUGH
FUCHSIA FILTER

BALANCED SPECTRUM
THROUGH
FUCHSIA FILTER

LIGHT TESTING AND STIMULATING DEVICE EMPLOYING VARIABLE FREQUENCY INTERRUPTED LIGHT SOURCE AND COLOR FILTERS

This application is a continuation of application Ser. No. 07/06,891 filed 06-15-1987 and now abandoned.

BACKGROUND—FIELD OF INVENTION

This invention relates to optical instrumentation, particularly to an instrument which tests and therapeutically stimulates the neurovisual system by visible light.

BACKGROUND—DESCRIPTION OF PRIOR ART

There have been many previous devices used to shine visible light into the eyes for therapeutic purposes. These devices have been used to treat amblyopia, photophobia, learning disabilities, dyslexia, headaches, hyperactivity, fatigue, and many other problems. These devices have consisted of a housing which contains a light source, color filters, and a viewing area. As a person looks into the viewing area, the light source emits light which passes through the color filters into the viewer's eyes. The object is to be able to produce specific wavebands of colored light which will act as a stimulus to the neurovisual system.

Different waveband stimuli have been used for different patient conditions, as is known by those schooled in the art.

Heretofore, users of these devices regarded them as unsatisfactory because of three major problems.

The first problem was that of unsatisfactory therapuetic effectiveness due to untrue color stimuli created from the incandescent source used in all of the prior art devices. Incandescent lamps do not create a natural, balanced color spectrum. They produce a disproportionate high irradiance at the red end of the spectrum and a disproportionate low irradiance at the blue end of the spectrum (FIG. 7). Since a color filter can only pass the color emitted by the light source, a disporportionate light emission produces disproportionate, untrue colors, and thus inferior, and sometimes totally ineffective, therapeutic color stimuli. For example, it is inherent in a yellow glass filter that it not only passes yellow, but it also passes orange and red. To get the effect of yellow as a therapeutic stimulus, the irradiance should peak in the yellow part of the spectrum. However, an incandescent light source peaks in the red (FIG. 8). Thus if the prior art devices were adjusted to give a subject a needed yellow stimulus, the subject was actually getting the effect of a red stimulus with diminished therapeutic results. A second example is seen with a fuchsia filter which passes an equal amount of deep red at one end of the spectrum and violet at the opposite end of the spectrum. the incandescent source of prior art devices emits so little violet that the actual stimulatory effect of the prior art fuchsia filter was that of red (FIG. 9) which made the fuchsia stimulus totally ineffective therapeutically. As can be seen from FIG. 7, the incandescent source emits so little blue and violet that the those prior art blue and violet filters were also very poor therapeutic stimulators.

The second problem users had was the biological inactiveness of photons generated from the prior arts incandescent light source. Even when a true color stimulus could be obtained, which was possible with a red filter, for example, therapy was still ineffective with many subjects.

The third problem was that users had to make a subjective determination of the needed color stimulus. It was true that users were schooled in the art, and did know basic rules of thumb for color stimulus prescribing, such as the use of red as a sensory stimulus to counteract amblyopia, and the use of blue as a sensory depressant to counteract headaches. However, many subjects had conflicting symptoms, for example amblyopia with a headache. In those cases, it was impossible to determine with accuracy the color stimulus needed. T.e., prior art lacked an objective test for determining proper color stimuli.

OBJECTS AND ADVANTAGES

Accordingly, several objects and advantages of my invention are: to provide an improved light stimulator device for rehabilitating the neurovisual system, to provide a light source which produces a balanced color spectrum and thus creates truer and more effective color stimuli, to provide an improved light source which produces more effective, biologically active photons, and to provide a mechanism which objectively determines the correct color stimulus for a given subject. Further objects and advantages will become apparent from the ensuing description and accompanying drawings.

Figure 1:
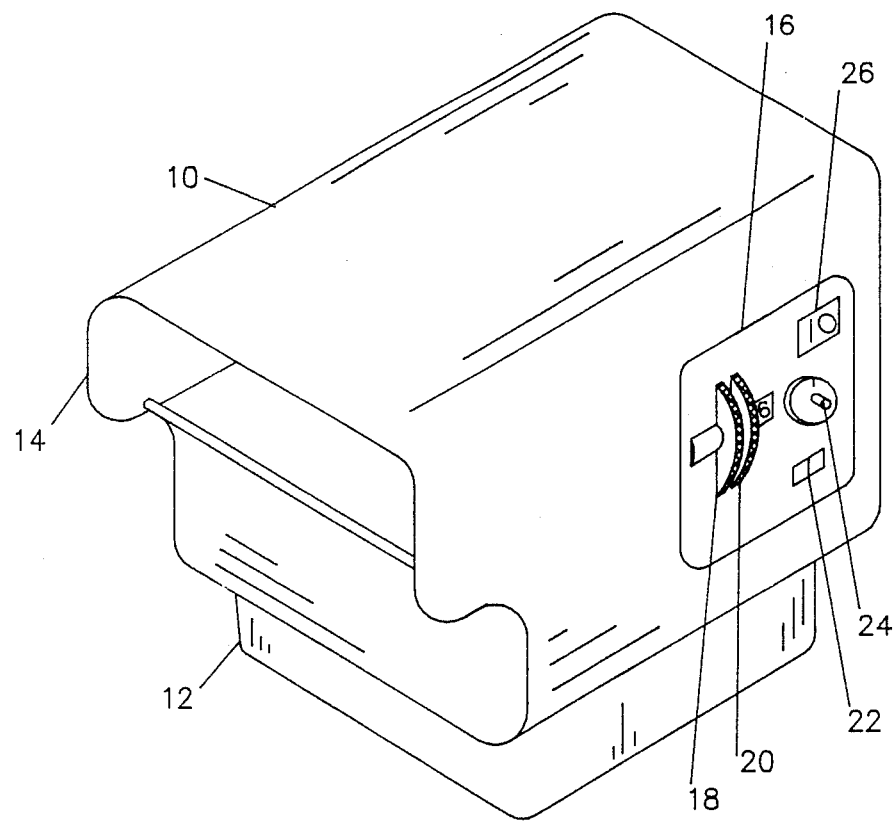
FIG. 1 shows a perspective side view of a light stimulator according to the invention.

DRAWING REFERENCE NUMERALS 10 housing
12 base
14 open front
15 eyes of subject
16 control panel
18 aperture wheel
20 color filter wheel
21 axis pin
22 power switch
24 flash rate control dial
26 flash rate display
28 light path
29 collimating lens holder
30 collimating lens
31 inner wall
32 light source
33 safety collar 34 light source power circuit
35 safety filters
36 glass envelope
38 glass discharge tube
42 anode
44 cathode
46 large viewing aperture
48 small CFF test aperture
50 motorized shutter
52 electromagnet

LIGHT STIMULATOR—DESCRIPTION

FIG. 1 shows a perspective side view of an improved light stimulator according to a preferred embodiment of the invention. The improved light stimulator consists of a housing 10 (76 cm long, 46 cm wide, and 46 cm high) which sits on a base 12 (30 cm long, 30 cm wide, and 11 cm high) and has an open front 14 which serves as a viewing area whereby the eyes 15 (FIG. 2) of the subject 15 look over a distance of about 48 cm to a collimating lens 30. A control panel 16 exposes the edges of an aperture wheel 18 and color filter wheel 20. Their edges can be grasped so as to turn the wheels around an axis pin 21.

Figure 4:
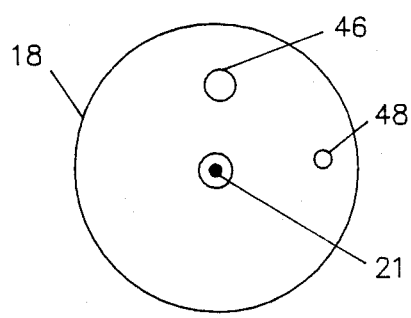
FIG. 4 shows a front view of an aperture wheel used in light stimulator.

Aperture wheel 18, shown in FIg. 4, is circular (35.5 cm in diameter) an contains a large viewing aperture 46 (2.5 cm in diameter) for use when a full therapeutic stimulus is needed. It also contains a small CFF (Critical Flicker Fusion) testing aperture 48 (1 mm in diameter) for use in testing the viewer's CFF for a given color. CFF is the flash rate (flashes per second) at which a flashing light with a gradually increasing flash rate first appears to be steady to a subject viewing the light. That is, the flashes will appear to fuse. When aperture wheel 18 is turned, it pivots around axis pin 21 and the selected aperture is brought into alignment with a light path 28 and held into position by detents (not shown) in wheel 18.

Figure 5:
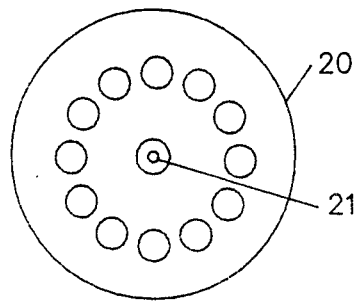
FIG. 5 shows a front view of a filter wheel used in such light stimulator.

Color filter wheel 20, shown in FIG. 5, is circular (35.5 cm in diameter) and contains twelve color filters which are: white, ruby, red, orange, yellow, yellow green, green, blue green, blue, indigo, violet, and fuchsia. When wheel 20 is turned, it pivots around axis pin 21 and the selected color filter is brought into alignment with light path 28 and held into position by detents (not shown) in color filter wheel 20.

Control panel 16 also holds a power switch 22 which turns on a light source 32 (see FIG. 2), a flash rate control dial 24 which adjusts the flash rate of light source 32 from 5 Hz to 55 Hz, and a digital flash rate display 26 (LED or other suitable readout) which indicates the flash rate to 0.1 Hz.

Figure 2:
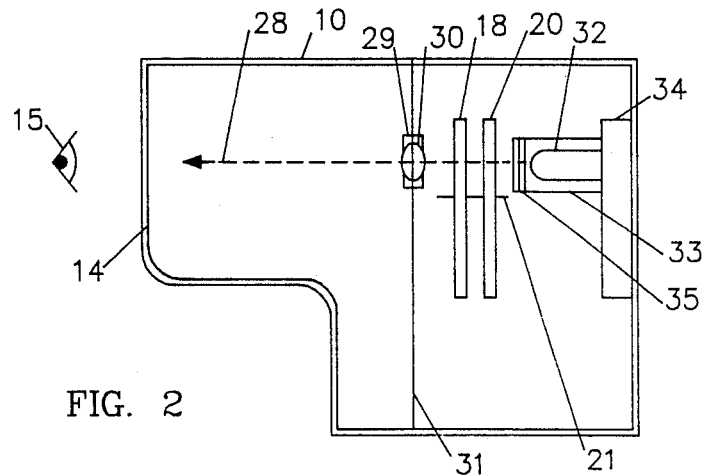
FIG. 2 shows a side view of the inside of such light stimulator.

FIG. 2 shows a side view of the inside of the improved light stimulator taken from its right side as seen by the eyes of subject 15 and assuming control panel 16 and the entire right side were removed. Light source 32, which produces light which travels along light path 28, is attached to and powered by a light source power circuit 34. Light path 28 first passes through safety filters 35, which consist of a UV (ultra violet) blocking filter which screens from the light path 28 all UV light and a neutral density filter which uniformly reduces any excess irradiance so that the maximum light intensity at the point just after leaving safety filters 35 is 11 lumens sec/Ft squared. Safety filters 35 are held in place by a safety collar 33. Light path 28 then passes through color filter wheel 20, then aperture wheel 18, then collimating lens 30 (a convex lens of approximately 18 diopters) which makes the light rays parallel, and continues into eyes of subject 15. Collimating lens 30 is held by a collimating lens holder 29 which is attached to an inner wall 31. The distance between light source 32 and collimating lens 30 is approximately 10 cm.

Figure 3:
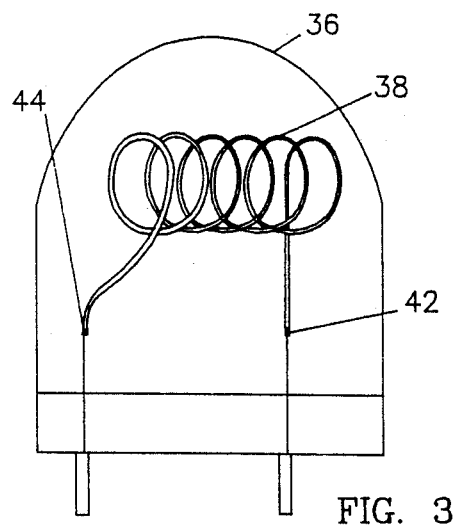
FIG. 3 shows an enlarged side view of a light source used in such light stimulator.

Light source 32 is detailed in FIG. 3. A glass envelope 36 encloses a glass discharge tube 38 which is coiled in seven multiple turns and contains gas, preferably a mixture which produces a full, balanced spectrum of light, approximating the light spectrum of sunlight at sea level at midday. This type of tube is available as model #FX-94c from Electro-Optics, Salem, Mass, U.S.A. Such gas is in contact with an anode 42 and a cathode 44 at opposite ends of tube 38. Both electrodes are attached to and powered by light source power circuit 34, available as model TM-12A from EG & G Electro-Optics. When light source power circuit 34 is turned on by power switch 22 (shown in FIG. 1), the gas inside glass discharge tube 38 ionizes to create plasma which emits light. The multiple turns in glass discharge tube 38 increase the magnetic field within the plasma. This increase in magnetism is due to the principle of electromagnetism that coiling an electrical current pathway increases the magnetic field associated with the current. Light source power circuit 34 supplies high-voltage pulses to glass discharge tube 38 so as to create light pulses at a rate of 5 Hz to 55 Hz. This flash rate can be continuously and precisely varied in increments of 0.1 flash per second.

Figure 6:
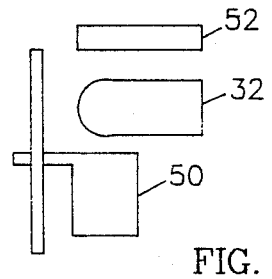
FIG. 6 shows an exposed side view of a light source, an optional electromagnet, and an optional motorized shutter used in such light stimulator.

The preferred embodiment of this invention provides a controllable, continuously variable flash rate produced by an electrical start and stop mechanism within light source power circuit 34. An alternative method would be the use of a motorized shutter 50 in front of light source 32, as shown FIG. 6. The preferred embodiment of this invention provides for a self-generating magnetic field within light source 32 by placing multiple coils in the glass discharge tube 38. An alternative method to create a magnetic field which encompasses light source 32 would be an adjacent elelctromagnet 52, as shown in FIG. 6. Other embodiments of this invention would include different aperture sizes and shapes in aperture wheel 18, a motorized aperture holder in place of aperture wheel 18, a motorized color filter holder in place of color filter wheel 20, and any light source which could be interrupted at a controllable, variable rate in conjunction with the use of color filters.

LIGHT STIMULATOR—OPERATION

To operate this improved light stimulator, power switch 22 is turned on, activating light source 32. An operator adjusts flash rate control dial 24 to a flash rate of 10.5 Hz, indicated by display 26.

To determine the proper therapeutic color stimulus, the operator performs the following steps:
(1) Adjust aperture wheel 18 so as to position small CFF testing aperture 48 in light path 28.
(2) Adjust color filter wheel 20 so as to position the first color filter (ruby) in light path 28.
(3) Adjust dial 24 to provide a flash rate of approximately 10.5 Hz.
(4) Place eyes of subject 15 at beginning of open front 14 and have the subject look at collimating lens 30.
(5) Ask the subject to say "now" when the flashing light appears to stop flashing and shine steadily.
(6) Gradually and continuously increase the flash rate until the subject says "now".

(7) Record the flash rate at this "now" point. This is the subject's CFF for this color.
(8) Repeat this procedure for all the colors contained in color filter wheel 20 except white. White is used only in conjunction with auxillary filters placed directly on eyes of subject 15. The white filter is included in this device for research only for those operators schooled in the art.

The color at which the subject has the lowest CFF is the color which that subject needs as a therpeutic stimulus.

The same results may alternatively be obtained by starting at a 55 Hz flash rate where the subject initially sees the light as steady and gradually reduce the flash rate to the point where the subject sees it as flickering. This point would then be recorded as the subject's CFF for that color.

To operate the improved light stimulator in its therapeutic mode, the operator performs the following steps:
(1) Adjust wheel 18 so as to position large viewing aperture 46 in light path 28.
(2) Adjust color filter wheel 20 so as to position the indicated color filter which the subject needs as a color stimulus in light path 28.
(3) Adjust flash rate control dial 24 to a flash rate of approximately 10.5 Hz.
(4) Place eyes of subject 15 at beginning of open front 14 and have the subject look at collimating lens 30.

This irradiates the subject's eyes with the indicated therapeutic color, causing his or her neurovisual pathways to be stimulated and rehabilitated to normal functioning.

Figure 7:
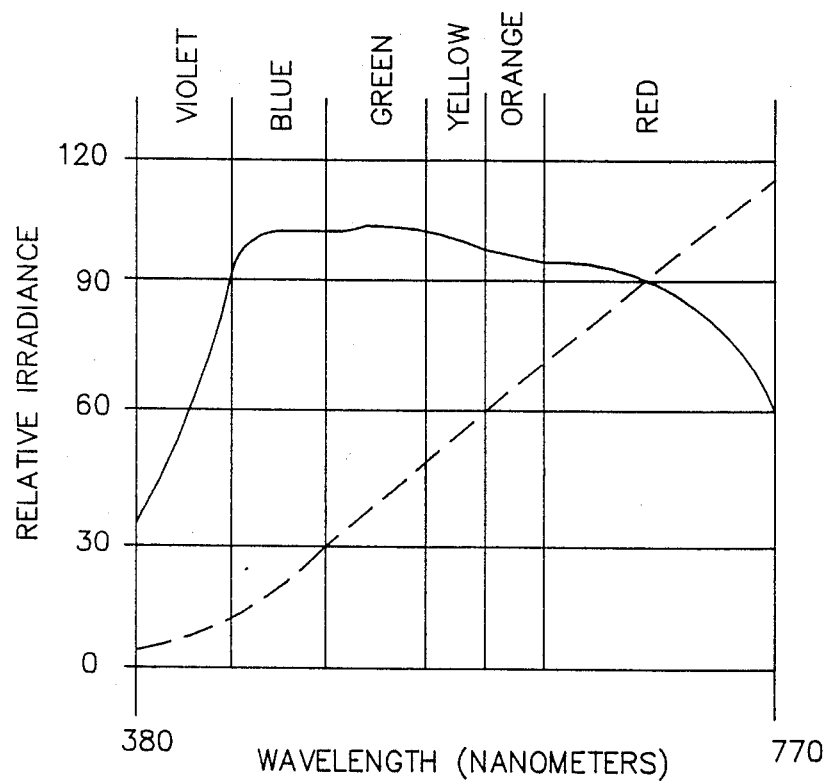
FIG. 7 shows a graph of the visible spectrum of the sun and an incandescent lamp.
Figure 8:
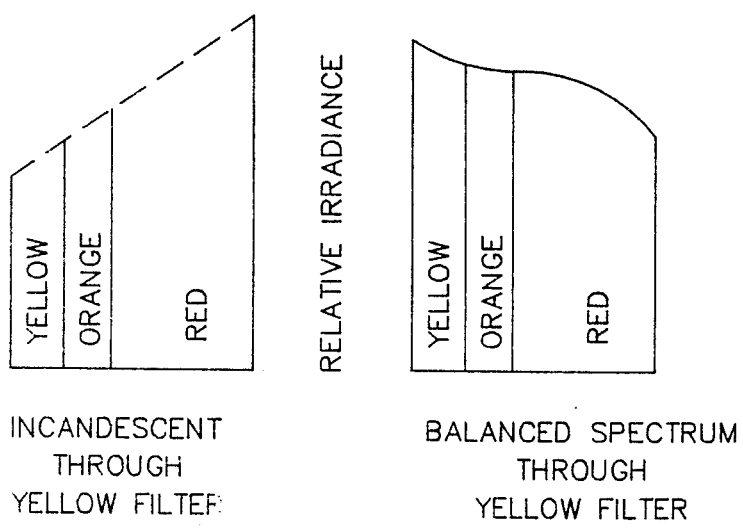
FIG. 8 shows a graph of the relative irradiance from incandescent and balanced-spectrum light sources through a yellow filter.
Figure 9:
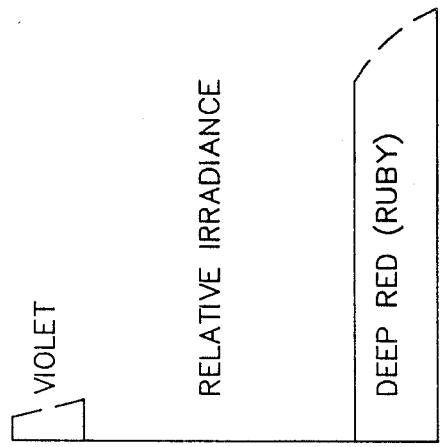
FIG. 9 shows a graph of the relative irradiance from incandescent and balanced-spectrum light sources through a fuchsia filter.
Figure 9:
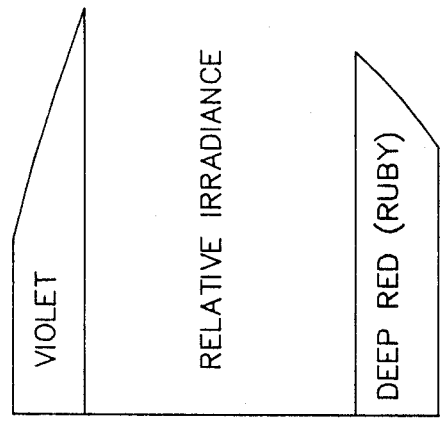

There are several factors which make my device an improvement over the prior art light stimulators:

Prior art light stimulators produced unsatisfactory therapeutic effectiveness due to untrue color stimuli created from the incandescent light source used. Incandescent lamps do not create a natural, balanced color spectrum, as indicated in FIG. 7. This produces disproportionate irradiance at different wavelengths within a band of color and therefore the corresponding photoreceptors in the retina do not get the amount of stimulus needed for adequate therapeutic effects, as indicated in FIGS. 8 and 9. My improved light stimulator uses a balanced spectrum light source comparable to sunlight (FIG. 7). This creates true colors which corresponded directly with the targeted retinal receptors and therefore create a much greater therapeutic effect (FIG. 8 and FIG. 9).

The second problem users found with prior art devices was again related to the incandescent light source. Even when a true color stimulus could be obtained, which was possible with some color filters, like the red filter for example, therapy was still ineffective with many subjects. The incandescently-created photons did not have the strong therapeutically stimulating effect which was needed. My improved light stimulator uses a plasma light source which I have empirically verified to create photons which produce much better therapeutic results. The multiple turns in the glass discharge tube increase the magnetic field within the plasma which I have also observed to further add to the therapeutic effectiveness of the photons emitted. Although not wishing to be bound, I believe that photons created out of a natural, magnetic, plasmatic environment, similar to that produced by sunlight and my light source, have an intensified subtle biomagnetic field surrounding them that present technology has not yet been able to measure. I futher believe that photons holding this biofield have a greater affinity to affect the human body by interaction with body's own biomagnetic field. This affinity might have developed over millions of years as humans have lived and evolved under the biological stimulus of sunlight. Whatever the reason, my magnetic, plasmatic light source produces a far greater therapeutic effect than the prior art incandescent sources. Plasma light sources and multiple coiled tubes have been used in other industries, such as photography, but they have never before been used in a therapeutic mode, especially to increase the effectiveness of light therapy.

The prior art devices contained no mechanism to objectively determine the correct waveband color stimulus for a given subject. My improved light stimulator device utilizes a test for CFF to determine the therapeutic color stimulus needed for a given subject. The CFF is a critical threshold which is directly linked to the functioning of the visual pathway. A low CFF for a given color stimulus indicates a diminished functioning of the neural pathway associated with that color's retinal receptor. I have found that stimulating the subject's eyes with the tested low CFF producing color stimulus will rehabilitate the diminished neural pathway, restoring its CFF to normal, and significantly reducing or eliminating the accompanying symptoms. Typical symptoms relieved are: amblyopia, photophobia, learning disabilities, headaches, and other visually related problems, etc. I have observed that the diminished neurovisual pathway can be re-educated by repetitive stimuli to proper functioning. The principle here is analagous to the "Law of Facilitation" which states that each succeeding nerve impulse meets with less resistance.

Flashing light sources were used in some prior art devices, but there has never before been a device that used a light source that had a controllable, continuously variable flash rate, or utilized a CFF test to determine the therapeutic stimuli.

CONCLUSION, RAMIFICATIONS, SCOPE

Thus the reader will see that the light stimulator of this invention provides for a more effective light stimulus than those of the prior art. This is because it produces a more natural, balanced color spectrum which creates more thereapeutically effective color stimuli. It produces a more effective, biologically active light by creating photons out of a natural, magnetic, plasmatic environment. It provides an objective CFF test for determining the correct color stimulus for a given subject.

While my above description contains many specificaties, these should not be construed as limitations on the scope of the invention, but rather as an exemplification of one preferred embodiment thereof. Many other variations are possible. For example, my invention can be made of any size, shape, color, material, or component combination. My invention can be used in any embodiment where a more biologically active light stimulus, either visible or invisible, is needed. My invention could be used to stimulate the whole or any part of a human, animal, plant, mineral, chemical composition, or any other material, matter, or substance. The light source used can be steady or flash at any rate. Accordingly, the scope of my invention should be determined not by the embodiment illustrated, but by the appended claims and their legal equivalents.

I claim:

1. A device for producing a therapeutic stimulus in a subject, comprising:
   a light source for shining light, at an effective level, into at least one eye of a subject,
   a plurality of color filters, each of said filters being arranged to transmit light which is of a single color only and which is different from the light transmitted by all of the other filters of said plurality,
   selection means for selectively interposing any one of said plurality of color filters between said light source and said eye of said subject,
   interruption means, separate from and additonal to said selection means, for continuously interrupting said light source, while any selected one of said color filters is interposed between said light source and said eye of said subject, at a selectable rate which is lower than the critical flicker fusion frequency of said subject, such that said subject will see said light source as interrupted,
   control means for increasing the frequency at which said interruption means interrupts said light source until said subject can see said light source change from interrupted to continuous, and
   indicating means for indicating the rate at which said interruption means interrupts said light source.

2. The device of claim 1 wherein said interruption means comprises a motor-driven shutter positioned between said light source and said eye of said subject.

3. The device of claim 1 wherein said interruption means comprises means for electrically turning said light source on and off.

4. The device of claim 1 wherein said light source is arranged to emit a spectrum which approximates the light emission curve of sunlight as measured at sea level at midday.

5. The device of claim 1, further including aperture means for additionally selectively interposing any one of a plurality of apertures of different sizes and shapes into a field-stopping position between said light source and said eye of said subject.

6. The device of claim 5 wherein said aperture means comprises a motorized aperture holder.

7. The device of claim 1 wherein said selection means comprises a motorized filter holder.

8. The device of claim 1, further including magnetic means for providing a self-generating magnetic field within said light source.

9. The device of claim 1 wherein said light source is arranged to illuminate both eyes of said subject.

10. The device of claim 1, further including magnetic means for providing a magnetic field which embraces said light source.

11. A device for producing a therapeutic stimulus in a subject, comprising:
    a light source and means for causing light from said source to illuminate at least one eye of a subject at an effective level, said light source being arranged to emit a spectrum which approximates the light emission curve of sunlight at sea level at midday,
    a plurality of color filters, each of which is arranged to transmit light which is of a single color only and which is different from the light transmitted by all of the other filters of said plurality,
    filter means for selectively interposing any one of said plurality of color filters between said light source and said eye of said subject,
    interruption means, separate from and additional to said selectioni means, for continuously interrupting said light source, while any selected one of said color filters is interposed between said light source and said eye of said subject, at a selectable rate which is higher than the critical flicker fusion frequency of said subject, such that said subject will see said light source as continuous, and
    control means for decreasing the frequency at which said interruption means interrupts said light source until said subject can see said light source change from continuous to interrupted, and
    indicating means for indicating the rate of interruption of said light source.

12. The device of claim 11 wherein said interruption means comprises a motor-driven shutter positioned between said light source and said eye of said subject.

13. The device of claim 11 wherein said interruption means comprises means for electrically turning said light source on and off.

14. A method for therapeutically stimulating a subject, comprising the following steps:
    (a) providing a plasma light source,
    (b) providing a set of color filters having respectively different colors between said light source and said subject, and selecting one of said color filters for use with said subject,
    (c) continuously interrupting said light source at a slow enough rate for said subject to see the interruptions of said light source and gradually increasing said rate until said subject perceives said light source as continuous, and
    (d) measuring and recording the rate of said interruptions at which said subject perceives said light source as continuous,
    whereby the rate recorded when said subject perceives said light source as continuous will be said subject's critical flicker fusion frequency for said selected one of said color filters.

15. The method of claim 14, further comprising repeating said steps (b) to (d) with color filters of different colors.

16. The method of claim 15, furhter comprising illuminating the eyes of said subject with light of the color having the lowest critical flicker fusion frequency for said subject.

17. The method of claim 16 wherein said illuminating is performed by interposing, between said light source and said subject, a filter of the color having the lowest critical flicker fusion frequency for said subject.

18. The device of claim 14 wherein said light source is arranged to emit a spectrum which approximates the light emission curve of sunlight as measured at sea level at midday.

19. A method for therapeutically stimulating a subject, comprising the following steps:
    (a) providing a plasma light source,
    (b) providing a set of color filters having respectively different colors between said light source and said subject, and selecting one of said color filters for use with said subject,
    (c) continuously interrupting said light source at a fast enough rate for said subject to see said light source as continuous and gradually decreasing said rate until said subject perceives the interruptions of said light source, and
    (d) measuring and recording the rate at which said subject perceives the interruptions of said light source, whereby the rate recorded when said subject perceives the interruptions of said light source will be said subject's critical flicker fusion frequency for said selected one of said color filters.

20. The method of claim 19, further comprising repeating said steps (b) to (d) with color filters of different colors.

21. The method of claim 20, further comprising illuminating the eyes of said subject with light of the color having the lowest critical flicker fusion frequency for said subject.

22. The method of claim 21 wherein said illuminating is performed by interposing, between said light source and said subject, a filter of the color having the lowest critical flicker fusion frequency for said subject.

23. The device of claim 19 wherein said light source is arranged to emit a spectrum which approximates the light emission curve of sunlight as measured at sea level at midday.

24. A method for therapeutically stimulating a subject, comprising the following steps:
   (a) providing light capable of providing any one of a plurality of different, single colors,
   (b) selecting a single one of said colors and shining light of said single, selected color into an eye of a subject,
   (c) continuously interrupting said light of said selected color at a slow enough rate for said subject to see said light of said selected color as interrupted,
   (d) gradually increasing the rate of interruption of said light of said selected color until said subject sees said light of said selected color change from interrupted to continuous, and
   (d) measuring and recording the rate at which said subject perceives said light of said selected color as continuous, whereby the rate recorded when said subject perceives said light of said selected color as continuous will be said subject's critical flicker fusion frequency for said light of said selected color.

25. A method for therapeutically stimulating a subject, comprising the following steps:
   (a) providing light capable of providing any one of a plurality of different, single colors,
   (b) selecting a single one of said colors and shining light of said single, selected color into said eye of said subject,
   (c) continuously interrupting said light of said selected color at a fast enough rate for said subject to see said light of said selected color as continuous,
   (d) gradually decreasing the rate of interruption of said light of said selected color until said subject sees said light of said selected color change from continuous to interrupted, and
   (d) measuring and recording the rate at which said subject perceives said light of said selected color as interrupted, whereby the rate recorded when said subject perceives said light of said selected color as interrupted will be said subject's critical flicker fusion frequency for said light of said selected color.

* * * * *